United States Patent
Sugita et al.

(10) Patent No.: US 10,314,834 B2
(45) Date of Patent: Jun. 11, 2019

(54) THERAPEUTIC AGENT OR TREATMENT METHOD FOR PHILADELPHIA CHROMOSOME-POSITIVE (PH+) ACUTE LYMPHOCYTIC LEUKEMIA (ALL) HAVING IKZF1 MUTATION

(71) Applicants: UNIVERSITY OF YAMANASHI, Yamanashi (JP); TOKAI UNIVERSITY EDUCATIONAL SYSTEM, Tokyo (JP)

(72) Inventors: Kanji Sugita, Yamanashi (JP); Kiyoshi Ando, Kanagawa (JP)

(73) Assignees: UNIVERSITY OF YAMANASHI, Yamanashi (JP); TOKAI UNIVERSITY EDUCATIONAL SYSTEM, Tokyo (JP)

( * ) Notice: Subject to any disclaimer, the term of this patent is extended or adjusted under 35 U.S.C. 154(b) by 0 days.

(21) Appl. No.: 15/758,582

(22) PCT Filed: Sep. 9, 2016

(86) PCT No.: PCT/JP2016/076636
§ 371 (c)(1),
(2) Date: Mar. 8, 2018

(87) PCT Pub. No.: WO2017/043633
PCT Pub. Date: Mar. 16, 2017

(65) Prior Publication Data
US 2018/0243284 A1 Aug. 30, 2018

(30) Foreign Application Priority Data
Sep. 10, 2015 (WO) .................. PCT/JP2015/075773

(51) Int. Cl.
| | |
|---|---|
| *A61K 31/454* | (2006.01) |
| *A61K 45/00* | (2006.01) |
| *A61K 31/122* | (2006.01) |
| *A61K 31/167* | (2006.01) |
| *A61K 31/404* | (2006.01) |
| *A61K 31/437* | (2006.01) |
| *A61K 31/4439* | (2006.01) |
| *A61K 31/444* | (2006.01) |
| *A61K 31/496* | (2006.01) |
| *A61K 31/502* | (2006.01) |
| *A61K 31/5025* | (2006.01) |
| *A61K 31/506* | (2006.01) |
| *A61K 31/517* | (2006.01) |
| *A61K 31/553* | (2006.01) |

(52) U.S. Cl.
CPC .......... *A61K 31/454* (2013.01); *A61K 31/122* (2013.01); *A61K 31/167* (2013.01); *A61K 31/404* (2013.01); *A61K 31/437* (2013.01); *A61K 31/444* (2013.01); *A61K 31/4439* (2013.01); *A61K 31/496* (2013.01); *A61K 31/502* (2013.01); *A61K 31/506* (2013.01); *A61K 31/5025* (2013.01); *A61K 31/517* (2013.01); *A61K 31/553* (2013.01); *A61K 45/00* (2013.01)

(58) Field of Classification Search
CPC ........................... A61K 31/495; A61K 31/454
See application file for complete search history.

(56) References Cited

U.S. PATENT DOCUMENTS

| | | | |
|---|---|---|---|
| 2012/0244116 A1* | 9/2012 | Hiwase ................ | A61K 31/122 424/85.2 |
| 2015/0093355 A1 | 4/2015 | Hiwase et al. | |
| 2016/0304616 A1 | 10/2016 | Hiwase et al. | |

FOREIGN PATENT DOCUMENTS

JP    2013-505968 A    2/2013

OTHER PUBLICATIONS

Weissinger et al., Onkologe, 2007, 13(3): 213-226 (include English translated version).*
Hurtado-Monroy et al., Clinical Lymphoma & Leukemia, 2013, 13: S385-S386.*
International Search Report dated Nov. 8, 2016 of corresponding International application No. PCT/JP2016/076636; 5 pgs.
JM Boer et al., "Prognostic value of rare IKZFJ deletion 1n childhood B-cell precursor acute lymphoblastic leukemia: an international collaborative study", Leukemia (2016) 30, pp. 32-38.
Charles G. Mullighan et al., "Deletion of IKZF1 and Prognosis in Acute Lymphoblastic Leukemia", The New England Journal of Medicine, Jan. 29, 2009, pp. 470-480.
B. Rini et al., "A phase I/II study of lenalidomide in combination with sunitinib in patients with advanced or metastatic renal cell carcinoma", Annals of Oncology, Jun. 8, 2014, vol. 25, pp. 1794-1799.
Isabel Jungkunz-Stier et al., "Modulation of natural killer cell effector functions through lenalidomide/dasatinib and their combined effects against multiple myeloma cells", Leukemia & Lymphoma, Jan. 2014, vol. 55, Issue 1, pp. 168-176.
C. Offiah et al., "Co-existing chronic myeloid leukaemia and multiple myeloma: rapid response to lenalidomide during imatinib treatment", International J Hematol, 2012, vol. 95, pp. 451-452.

(Continued)

*Primary Examiner* — Rei Tsang Shiao
(74) *Attorney, Agent, or Firm* — Maier & Maier, PLLC (57) ABSTRACT

According to the present invention, there is provided a pharmaceutical composition for treating Philadelphia chromosome positive lymphocytic leukemia, including a thalidomide derivative and BCR-ABL tyrosine kinase inhibitor. According to the present invention there is also provided a method of treating Philadelphia chromosome positive lymphocytic leukemia, including administering a thalidomide derivative and a BCR-ABL tyrosine kinase inhibitor to a patient suffering from Philadelphia chromosome positive lymphocytic leukemia.

6 Claims, 6 Drawing Sheets

(56) References Cited

OTHER PUBLICATIONS

Rafael Hurtado-Monroy et al., "Chronic Myeloid Leukemia Philadelphia Chromosome Positive (CML Ph+) With Imatinib (IM) Intolerance or Resistant Disease—Response to Thalidomide (TALI) Treatment—Preliminary Report of a Serial of Cases With Encouraging Results", Clinical Lymphoma, Myeloma & Leukemia, Sep. 2013, vol. 13, Supplement 2, pp. S385-S386.

Rafael Hurtado-Monroy et al., "Imatinib (IM) Plus Thalidomide (Thali), A Effective Combination for the Treatment of Chronic Myeloid Leukemia (CML) Philadelphia ChromosomePositive (Ph +) in IM-Resistant Disease. Report of 14 New Cases From a Single Center in Mexico", Blood, 2013, vol. 122, Issue 21, p. 5172.

Ota Fuchs, "Transcription Factor NF-kB Inhibitors as Single Therapeutic Agents or in Combination with Classical Chemotherapeutic Agents for the Treatment of Hematologic Malignancies", Current Molecular Pharmacology, 2010, vol. 3, No. 3, pp. 98-122.

T. Braun et al., "Targeting NF-kB in hematologic malignancies", Cell Death and Differentiation, 2006, vol. 13, pp. 748-758.

Hui-Jen Tsai et al., "Bioimaging analysis of nuclear factor-kB activity in Philadelphia chromosome-positive acute lymphoblastic leukemia cells reveals its synergistic upregulation by tumor necrosis factor-α-stimulated changes to the microenvironment", Cancer Science, 2011, vol. 102, Issue 11, pp. 2014-2021, ISSN 1349-7006, particularly summary.

E. Tavernier-Tardy et al., haematologica, 2014, vol. 99, No. sI, p. 281, ISSN 0390-6078, entire text.

Atsushi Manabe, "Treatment of Philadelphia Chromosome-Positive Acute Lymphoblastic Leukemia", The Japanese Journal of Pediatric Hematology, 2008, vol. 22, pp. 306-311, ISSN 0913-8706, particularly p. 308, chapter III, p. 309, chapter VII, p. 310, chapter IX.

Daisuke Harama et al., "Lenalidomide induces apoptosis of Ph positive ALL cells in synergy with imatinib", The Japanese Journal of Clinical Hematology, Sep. 30, 2015, vol. 56, No. 9, p. 464 (1580), ISSN 0485-1439, entire text.

\* cited by examiner

THERAPEUTIC AGENT OR TREATMENT METHOD FOR PHILADELPHIA CHROMOSOME-POSITIVE (PH+) ACUTE LYMPHOCYTIC LEUKEMIA (ALL) HAVING IKZF1 MUTATION

BACKGROUND ART

Philadelphia chromosome positive acute lymphocytic leukemia (Ph+ALL) is an extremely refractory acute leukemia that cannot be cured by ordinary chemotherapies. In patients with Ph+ALL, fusion tyrosine kinases (BCR-ABL) with high activity are generated due to 9;22 chromosomal translocation.

Allogeneic hematopoietic stem cell transplantation has been the only way to cure Ph+ALL completely. However, the allogeneic hematopoietic stem cell transplantation has many problems to be addressed such as transplantation-related death, graft-versus-host disease and organ complication. Therefore, a new therapeutic strategy is needed to improve an outcome of treatment and maintain high quality of life (QOL) of the patients with Ph+ALL.

Recently, tyrosine kinase inhibitors (TKIs; imatinib, dasatinib, etc.), which are molecular targeted drugs for BCR-ABL, have been discovered and approved, resulting that prognosis has been improved by introducing them in actual treatment. However, its outcome has not reached to a satisfactory level yet.

Figure 1:
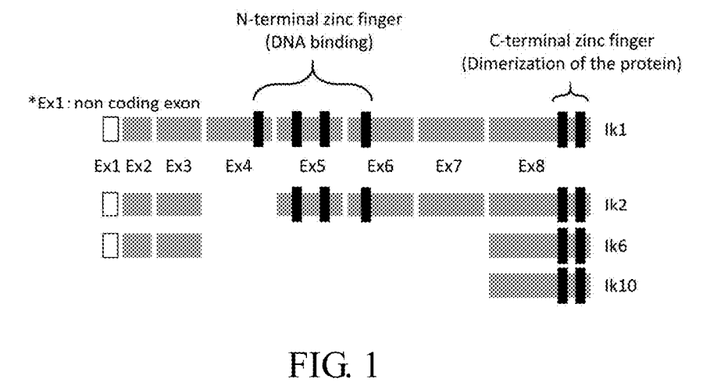
FIG. 1 shows structure of IKZF1 and its mutant isoform. An IKZF1 gene have eight exons, exons 4-6 being DNA binding domains, and exon 8 encoding a dimerization domain.

Ikaros family zinc finger protein 1 (IKZF1) is an essential transcription factor for differentiation of all lymphoid cells. An IKZF1 gene has eight exons, exons 4 to 6 being DNA binding domains, and exon 8 encoding a dimerization domain (FIG. 1). Recently, it has been clearly found that presence or absence of an IKZF1 gene mutation is the most important factor for determining prognosis for treatment of ALL (Non-Patent Document 1). That is, prognosis in ALL with the IKZF1 gene mutation (one allele mutation) is related to extremely poor. Highly frequent gene mutations are defects of exons 4 to 7 (DNA binding defect) and defects of exons 1 to 8 (complete defect). The former acts as a dominant-negative (dominant inhibitory) isoform (Ik6) which inhibits formation of normal dimer having transcriptional activity. The latter shows haploinsufficiency. Frequency of the IKZF1 gene mutation in the patient with Ph+ALL is about 80% which is very high, and Ph+ALL is closely related to poor prognosis (Non-Patent Document 2). On the other hand, frequency of the IKZF1 gene mutation in Ph-negative ALL is a small percent. Therefore, proportion of ALL with the IKZF1 gene mutation is regulated by frequency of Ph+, and it has been reported that pediatric patients with low frequency of Ph+ are less than 15% and adult patients with high frequency of Ph+ is about 40%.

Derivatives with reduced toxicity of thalidomide such as lenalidomide and pomalidomide have various biological activities, which are referred to collectively as immunomodulators (IMiDs). These derivatives have been shown to be effective in treatment of multiple myeloma and certain myelodysplastic syndromes, and have already been clinically applied. Clinical trials of the thalidomide derivatives against malignant lymphoma, adult T cell leukemia lymphoma and the like are under way in the United States. However, effects of the thalidomide derivatives on ALL have not been fundamentally investigated so far. Therefore, no clinical trials for the thalidomide derivatives on ALL have been conducted.

Non-patent document 3 discloses that clinical trial to use lenalidomide and sunitinib against renal cell carcinoma was performed. Non-patent document 4 discloses that lenalidomide and dasatinib are used against multiple myeloma. Non-patent document 5 reports that treatment to use imatinib and lenalidomide was effective in multiple myeloma patients who developed chronic myelogenous leukemia at the same time as a rare case. Non-patent document 6 discloses that treatment of chronic myelogenous leukemia was performed by using imatinib and thalidomide. Non-patent document 7 discloses that treatment of chronic myeloid leukemia was performed by using imatinib and thalidomide. Non-patent documents 8 and 9 outline the significance of NFkB inhibitors for hematologic malignancies with high NFkB activity, such as multiple myeloma and chronic myelogenous leukemia.

Patent Document 1 discloses a method of treating a patient with Ph+ leukemia by using a BCR-ABL tyrosine kinase inhibitor and a drug for injection which selectively binds to various cytokine receptors (IL-3R, G-CSFR, GM-CSFR) expressed outside (on cell surface of) leukemic cells.

PRIOR ART DOCUMENTS

Patent Document

Patent Document 1: JP2013-505968A

Non-Patent Document

Non-Patent Document 1: J M Boer et al. Leukemia 2016, 30: 32-38
Non-Patent Document 2: C G Mullighan. N Engl J Med 2009. 29: 470-480
Non-Patent Document 3: RINI, B. et al., Annals of Oncology, 2014.06, Vol. 25, pp. 1794-1799
Non-Patent Document 4: JUNGKUNZ-STIER, Isabel et al., Leukemia & Lymphoma, 2014, Vol. 55, Issue 1, pp. 168-176
Non-Patent Document 5: OFFIAH, C et al., International Journal of Hematology, 2012, Vol. 95, Issue 4, pp. 451-452
Non-Patent Document 6: HURTADO-MONROY, Rafael et al., Clinical Lymphoma, Myeloma & Leukemia, 2013, Vol. 13, Supplement 2, pp. S385-S386
Non-Patent Document 7: HURTADO MONROY, Rafael et al., Blood, 2013, Vol. 122, Issue 21, p. 5172
Non-Patent Document 8: O T A Fuchs, Current Molecular Pharmacology, 2010, Vol. 3, No. 3, pp. 98-122
Non-Patent Document 9: BRAUN, Tal et al., Cell Death and Differentiation, 2006, Vol. 13, pp. 748-758

SUMMARY OF THE INVENTION

Problem to be Solved by the Invention

However, the prior arts described above have room for further improvement in the following points.

In the non-patent document 3, a target disease is not leukemia, and there is no description about treatment of Ph+ALL with an IKZF1 mutation. In addition, the non-patent document 3 fails to disclose that sunitinib is used to treat leukemia.

In the non-patent document 4, a target disease is not leukemia, and there is no description about the treatment of Ph+ALL with the IKZF1 mutation. In addition, the non-patent document 7 mainly studies effect of a therapeutic agent on NK cell function.

The non-patent document 5 only discloses that imatinib is used as a therapeutic agent for multiple myeloma and lenalidomide is used as a therapeutic agent for chronic myelogenous leukemia, and fails to disclose the treatment of Ph+ALL with the IKZF1 mutation.

The non-patent documents 6 and 7 only disclose that chronic myeloid leukemia was treated with imatinib and thalidomide, and fails to disclose the treatment of Ph+ALL with the IKZF1 mutation. It is also widely known that chronic myelogenous leukemia does not have the IKZF1 mutation.

The non-patent documents 8 and 9 outline significance of NFkB inhibitors against blood malignancies with high NFkB activity (e.g., multiple myeloma and chronic myelogenous leukemia). However, none of the documents describes the treatment of Ph+ALL with the IKZF1 mutation. In addition, the NFkB activity is not enhanced in Ph+ALL, whereas the IKZF1 mutation is not observed in multiple myeloma and chronic myelogenous leukemia.

In the patent document 1, a target case is chronic myelogenous leukemia (without the IKZF1 mutation), and treatment method thereof was cumbersome because of use of a drug for injection and a tyrosine kinase inhibitor as an internal medicine.

Means of Solving the Problems

The present inventors studied effect of combination of lenalidomide with TKIs (imatinib, dasatinib) in vitro in human Ph+ ALL cell strains (all with ab IKZF1 mutation). Lenalidomide alone or TKI alone showed moderate proliferation inhibitory effect. When lenalidomide and TKI were used in combination, a cell death inducing effect was shown and most cells died within one week in culture. As shown in examples described later, this effect was also demonstrated in in-vivo system in which human Ph+ALL cells were transplanted into immunocompromised mice (NOG mice). A clinical trial of lenalidomide to malignant lymphoma and adult T cell leukemia lymphoma have been conducted in the United States. However, effect of lenalidomide on ALL has not been investigated at all and clinical application has not been done. The inventors of the present invention have clarified, for the first time, that treatment outcomes and QOL of patients having Ph+ALL with an IKZF1 mutation can be remarkably improved by applying both drugs in combination (both internal medicine) in actual clinical practice, and then the present invention has been completed.

That is, according to the present invention, there is provided a pharmaceutical composition for treating Philadelphia chromosome positive lymphocytic leukemia, including a thalidomide derivative and a BCR-ABL tyrosine kinase inhibitor. According to this constitution, the composition can be used for treating Philadelphia chromosome positive lymphocytic leukemia. In addition, according to this constitution, the composition can be used for treating Philadelphia chromosome positive lymphocytic leukemia with an IKZF1 mutation. Furthermore, according to this constitution, the composition can be used for treating Philadelphia chromosome positive acute lymphocytic leukemia (Ph+ALL) with the IKZF1 mutation. In addition, the IKZF1 mutation is frequently found in Ph positive chronic myelogenous leukemia in lymphatic blast phase. Thus, the composition can be used for treating Ph positive chronic myelogenous leukemia in lymphoid in the blast phase as well as Ph+ALL.

According to the present invention, there is also provided a method of treating Philadelphia chromosome positive lymphocytic leukemia, including administering a thalidomide derivative and a BCR-ABL tyrosine kinase inhibitor to a patient suffering from Philadelphia chromosome positive lymphocytic leukemia. Philadelphia chromosome positive lymphocytic leukemia can be treated by applying this method to the patient suffering from such leukemia. In addition, Philadelphia chromosome positive lymphocytic leukemia with an IKZF1 mutation can be treated by applying this method to the patient suffering from such leukemia. Ph+ALL with the IKZF1 mutation can be treated by applying this method to the patient suffering from such leukemia. Ph positive chronic myelogenous leukemia in lymphatic blast phase can be also treated by applying this method to the patient suffering from such leukemia.

BRIEF DESCRIPTION OF THE DRAWINGS

FIGS. 3A and 3B show graphs showing that $H^3$-thymidine uptake was suppressed by incubating lenalidomide high sensitive Ph+ALL strain (KOPN57bi) in the presence of lenalidomide (LMD) alone, imatinib (IM) alone or combination thereof for 3 days. In FIG. 3A, concentrations of imatinib were varied. In FIG. 3B, concentrations of lenalidomide were varied.

FIG. 8 shows graphs showing proportion of activated caspase 3 which is an apoptosis-executing molecule, by using flow cytometry after culturing the lenalidomide high sensitive Ph+ALL cell strain (KOPN57bi) in the presence of lenalidomide (LMD, 20 μM) alone, imatinib (IM, 0.5 nM)

alone or combination thereof for 3 days. Numerals show percentage of activated caspase 3 positive cells.

FIGS. 10A and 10B show results of effect of dasatinib (DTB) which is a TKI other than imatinib. FIG. 10A shows a result of thymidine uptake after culturing the lenalidomide high sensitive Ph+ALL cell strain (KOPN57bi) in the presence of dasatinib (DTB) or imatinib (IM) for 3 days.

FIG. 11 shows change in expression of IKZF1 protein using a western blotting method after culturing the lenalidomide high sensitive Ph+ALL cell strain (KOPN57bi) in the presence of lenalidomide (LMD) alone, imatinib (IM) alone or combination thereof for 24 hours. No change was observed in expression of dominant-negative isoform (Ik 6) under the above conditions, whereas expressions of normal allele-derived complete protein and splicing isoform were completely found by addition of lenalidomide. It has been known that lenalidomide binds to its receptor, cerebron (with ubiquitin ligase activity) in cytoplasm, and its complex binds to exon 5 of the IKZF1 protein (glutamine residue at position 146). It is considered that when lenalidomide is administered to Ph+ALL with the IKZF1 mutation, the cerebron complex cannot bind to dominant-negative isoform lacking cerebron binding site, but binds to normal allele-derived IKZF1 protein only, resulting that the expression is not observed by ubiquitination.

DETAILED DESCRIPTION OF THE INVENTION

Hereinafter, embodiments of the present invention will be described in detail. In order to avoid cumbersome redundant description, the description of the same contents will be omitted as appropriate.

1. Philadelphia Chromosome Positive (Ph+) Lymphocytic Leukemia

Philadelphia chromosome positive (Ph+) lymphocytic leukemia (Ph+ lymphocytic leukemia) has Philadelphia chromosome positive (Ph+) acute lymphocytic leukemia (Ph+ALL) and Philadelphia chromosome positive (Ph+) chronic myelogenous leukemia (CML) in lymphatic blast phase. In an embodiment, Philadelphia chromosome positive lymphocytic leukemia may be Ph+ ALL. In the present embodiment, Philadelphia chromosome positive lymphocytic leukemia may have a mutation in an Ikaros family zinc finger protein 1 (IKZF1) gene. The IKZF1 gene has eight exons, exons 4-6 being DNA binding domains and exon 8 encoding a dimerization domain (FIG. 1). In the present embodiment, the IKZF1 gene mutation may lack one or more exons. In the present embodiment, the IKZF1 gene mutation may lack exon 5. In the present embodiment, the IKZF1 gene mutation may lack at least four exons. In the present embodiment, the IKZF1 gene mutation may lack at least four exons including exon 5. In the present embodiment, the IKZF1 gene mutation may lack exons 4-7. In the present embodiment, the IKZF1 gene mutation may lack exons 2-7. In the present embodiment, the IKZF1 gene mutation may have a single allelic mutation. In the present embodiment, the IKZF1 gene mutation may have both allelic mutations.

2. BCR-ABL Tyrosine Kinase Inhibitor

BCR-ABL tyrosine kinase inhibitors, which have been approved as therapeutic agents for chronic phase CML and Ph+ALL, are usually applied clinically as the therapeutic agents. The tyrosine kinase inhibitor include, for example, imatinib, dasatinib, nilotinib and bosutinib. The tyrosine kinase inhibitors may be used alone or in combination. Preferably, the tyrosine kinase inhibitor is imatinib (IUPAC: 4-(4-Methylpiperazin-1-ylmethyl)-N-[4-methyl-3-(4-pyridin-3-ylpyrimidin-2-ylamino) benzamide monomethanesulfonate. In treatment of Ph+ lymphocytic leukemia, a daily dose of the tyrosine kinase inhibitor may be 400 mg. Depending on age, weight and severity of a patient, a daily dose of the tyrosine kinase inhibitor may be 200 mg, 300 mg, 400 mg, 500 mg, 600 mg, 700 mg or 800 mg or in the range between two points selected from them.

3. Thalidomide Derivatives

Toxicity-reduced derivatives of thalidomide, which are collectively referred to as immunomodulators (IMiDs), have various biological activities. Recently, it has been found that the derivatives are effective for treatment of multiple myeloma and specific myelodysplastic syndrome. The derivatives has been approved for health, and are applied clinically. Examples of the thalidomide derivative include, but are not limited to, lenalidomide and pomalidomide. The thalidomide derivatives may be used alone or in combination. The thalidomide derivative is preferably lenalidomide (IUPAC: (RS)-3-(4-amino-1-oxo-3H-isoindol-2-yl) piperidine-2, 6-dione). Lenalidomide is clinically applied in multiple myeloma at a treatment schedule of 10-20 mg once a day for 3 weeks and 1 week rest. Toxicity of lenalidomide in single administration is known to the person skilled in the art. In treatment of Ph+ lymphocytic leukemia, a daily dose of thalidomide derivative may be 5 mg, 7 mg, 10 mg, 12 mg, 15 mg, 17 mg or 20 mg or in the range between two points selected from them, depending on age, weight and severity of a patient.

4. Pharmaceutical Composition for Treating Philadelphia Chromosome Positive Lymphocytic Leukemia, Including a BCR-ABL Tyrosine Kinase Inhibitor and a Thalidomide Derivative According to the present invention, there is provided a pharmaceutical composition for treating Philadelphia chromosome positive lymphocytic leukemia, including a BCR-ABL tyrosine kinase inhibitor and a thalidomide derivative. The BCR-ABL tyrosine kinase inhibitor and the thalidomide derivative may be administered in the form of a pharmaceutical composition. The pharmaceutical composition is manufactured under GMP conditions. The pharmaceutical composition may be in unit dosage form (i.e., dosage for single administration) containing any dosage amount as follows. The pharmaceutical composition may be prepared by conventional methods having mixing, dissolving, granulating, sugarcoating, levigating, emulsifying, encapsulating, entrapping or lyophilizing processes. In particular, the BCR-ABL tyrosine kinase inhibitor and thalidomide derivative may be used in the formulations and compositions as follows.

The pharmaceutical composition may be formulated in a conventional manner using one or more physiologically acceptable carriers, diluents, excipients or auxiliaries that facilitate processing the BCR-ABL tyrosine kinase inhibitor and the thalidomide derivative into a formulation that can be used for medical use. The appropriate formulation will depend on chosen administration route.

The pharmaceutical composition may be administered parenterally, intravenously, orally, subcutaneously, intraarterially, intracranially, intrathecally, intraperitoneally, topically, intranasally or intramuscularly. Oral administration is preferred.

The pharmaceutical composition for the parenteral administration is preferably sterile and substantially isotonic. For injection, the BCR-ABL tyrosine kinase inhibitor and the thalidomide derivative may be formulated in an aqueous solution, preferably physiologically compatible buffer such as Hank's solution, Ringer's solution, physiological saline or acetate buffer (for reduction of discomfort at the injection site). The solution may contain a modifier such as a suspending agent, a stabilizing agent, and/or a dispersing agent.

In addition, the BCR-ABL tyrosine kinase inhibitor and the thalidomide derivative may be in powder form for constitution with a suitable vehicle (e.g., sterile, pyrogen-free water) before use.

For transmucosal administration, penetrants appropriate to barrier to be permeated are used during the formulation. This administration route may be used for nasal administration or for sublingual administration of the BCR-ABL tyrosine kinase inhibitor and the thalidomide derivative.

For the oral administration by the patient to be treated, the BCR-ABL tyrosine kinase inhibitor and the thalidomide derivative may be formulated by combining with tablet, pill, sugar-coated tablet, capsule, liquid, gel, syrup, slurry, suspension or a pharmaceutically acceptable carrier as similar thereto. For example, for oral solid preparations such as powders, capsules and tablets, suitable excipients include fillers such as sugars (e.g., lactose, sucrose, mannitol and sorbitol); corn starch, wheat starch, rice starch, potato starch, gelatin, gum tragacanth, methylcellulose, hydroxypropylmethylcellulose, carboxymethylcellulose sodium and/or cellulose preparations such as polyvinylpyrrolidone (PVP); granules; and binders. If desired, disintegrating agents such as crosslinked polyvinylpyrrolidone, agar, or alginic acid or a salt thereof such as sodium alginate may be added. If required, solid dosage form may be sugar coated form or enteric coated form using standard techniques. For oral liquid preparations such as suspensions, elixirs and solutions, suitable carriers, excipients or diluents include water, glycol, oil or alcohol. In addition, fragrances, preservatives, coloring agents and the like may be added.

In addition to the formulations described above, the BCR-ABL tyrosine kinase inhibitor and the thalidomide derivative may also be formulated as a sustained release formulation. Such prolonged sustained release formulations may be administered by implantation (for example subcutaneously or intramuscularly) or by intramuscular injection. Thus, for example, the BCR-ABL tyrosine kinase inhibitor and the thalidomide derivative may be formulated with suitable polymers or hydrophobic materials (e.g., as an emulsion in an acceptable oil) or ion exchange resins, or as a moderate water-soluble derivative such as a moderate water-soluble salt.

Alternatively, other pharmaceutical delivery systems may be used. Liposomes and emulsion may be used to deliver the BCR-ABL tyrosine kinase inhibitor and the thalidomide derivative. Although possible to exhibit greater toxicity than usual, certain organic solvents such as dimethylsulfoxide may be used. In addition, these compounds may be delivered using a sustained release system such as a semipermeable matrix of a solid polymer containing a therapeutic agent.

5. Method of Treatment

According to the present invention, there is also provided a method of treating Philadelphia chromosome positive (ph+) lymphocytic leukemia, including administering a BCR-ABL tyrosine kinase inhibitor and a thalidomide derivative to a patient suffering from Philadelphia chromosome positive (ph+) lymphocytic leukemia. The patient may be a mammal, preferably a human. Philadelphia chromosome positive (Ph+) lymphocytic leukemia includes Philadelphia chromosome positive (Ph+) acute lymphocytic leukemia (Ph+ALL) and Philadelphia chromosome positive (Ph+) chronic myelogenous leukemia (CML) in lymphatic blast phase. Philadelphia chromosome positive (Ph+) lymphocytic leukemia is preferably Ph+ALL.

In this method of the treatment, the BCR-ABL tyrosine kinase inhibitor and the thalidomide derivative may be administered at the same time. In such a case, the inhibitor and the derivative may be administered as a combination agent, or administered as single agents at the same time. In addition, the inhibitor and the derivative may be administered at different times, and the order of administration is not particularly limited. The time difference may be, for example, 1 second, 5 seconds, 10 seconds, 1 minute, 5 minutes, 10 minutes, 30 minutes, 1 hour or 2 hours, or in the range between two points selected from them.

EXAMPLES

Hereinafter, the present invention will be further described with reference to examples and figures. However, the present invention is not limited thereto. Statistically significant means that p value is <0.05, preferably <0.01, and most preferably <0.001.

Example 1

Figure 2:
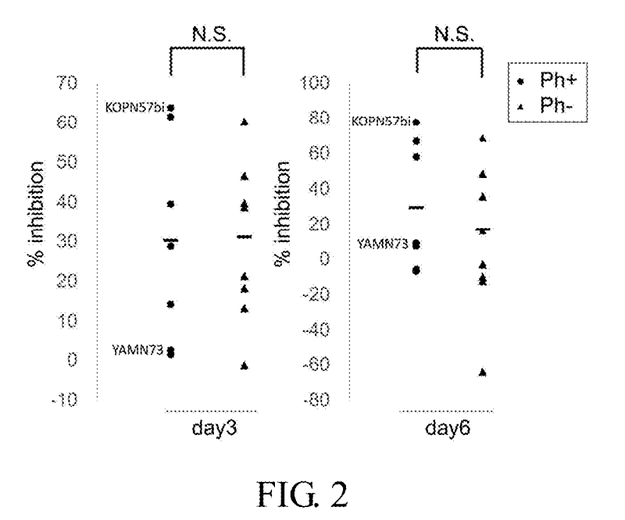
FIG. 2 shows results of influence on $H^3$-thymidine uptake on days 3 and 6 in culture in the case where lenalidomide (LMD) alone was added to seven Ph+ALL strains (all with an IKZF1 mutation) and eight Ph negative cell strains (all with normal IKZF1). There was no difference in an inhibition rate between Ph positive and negative strains. The Ph+ALL strain (KOPN57bi) lacking IKZF1 exons 4-7 showed a strong sensitivity to LMD and was widely used in the following examples.

Study on Effect of Lenalidomide Alone by Using a Tritium Cyimidine Uptake Method ($H^3$-Thymidine Uptake Method) (FIG. 2)

Influences on $H^3$-thymidine-uptake were examined by using various ALL cell strains treated with lenalidomide (LMD) alone. Using a 96-well culture plate, seven kinds of Ph+ALL strains (all with an IKZF1 mutation) and eight kinds of Ph negative cell strains (all with IKZF normal): 1; 19 translocated strains (n=2), 17; 19 translocated strains (n=2), MLL translocation strains (n=2) and 12; 21 translocation strains (n=2) were cultured in RPMI 1640 culture medium supplemented with 7.5% fetal bovine serum in the presence or absence of 20 μM LMD ($5\times10^4$ cells/well) for 3 or 6 days. Thereafter, $H^3$-thymidine (1 μCi, 6 hours) uptaken by each strain was measured and % inhibitions were calculated. In both groups, inhibition rates varied depending on the cell strains, and no difference in the inhibition rates was observed between the Ph positive strain and the negative strain. The inhibition rates (% inhibition) of the Ph+ALL strain KOPN57bi was about 65% for 3 days in the culture and about 80% for 6 days in the culture. The Ph+ALL strain KOPN57bi was used for experiments as a lenalidomide low sensitive strain.

Example 2

Study on Effect in Combination of Lenalidomide with Imatinib by Using a $H^3$-Thymidine Uptake Method (FIG. 3)

Figure 3A:
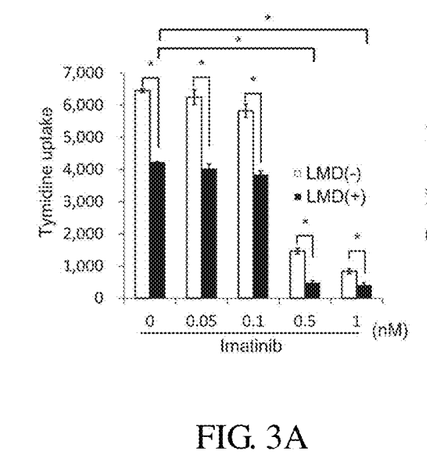
Figure 3B:
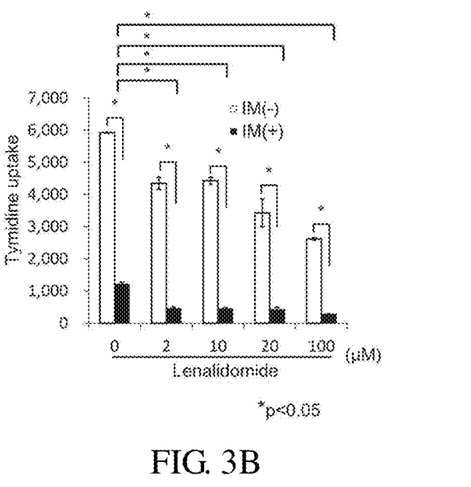

Using the Ph+ALL strain (KOPN57bi), effect in combination of LMD with imatinib (IM) was studied. The Ph+ALL strain (KOPN57bi) was cultured in the presence of 20 μM LMD alone, 0.5 μM IM alone or the combination thereof for 3 days, and then $H^3$-thymidine uptakes were measured. LMD and IM alone showed about 50% inhibition, whereas the combination of LMD with IM showed more than 90% inhibition. When the concentration of LMD was kept constant at 20 μM and the concentration of IM was 0.5 μM or more, % inhibition increased to 90% or more (FIG. 3A). When the concentration of IM was kept constant at 0.5 μM and the concentration of LMD was 2 μM or more, % inhibition increased to 90% or more (FIG. 3B).

Example 3

Figure 4:
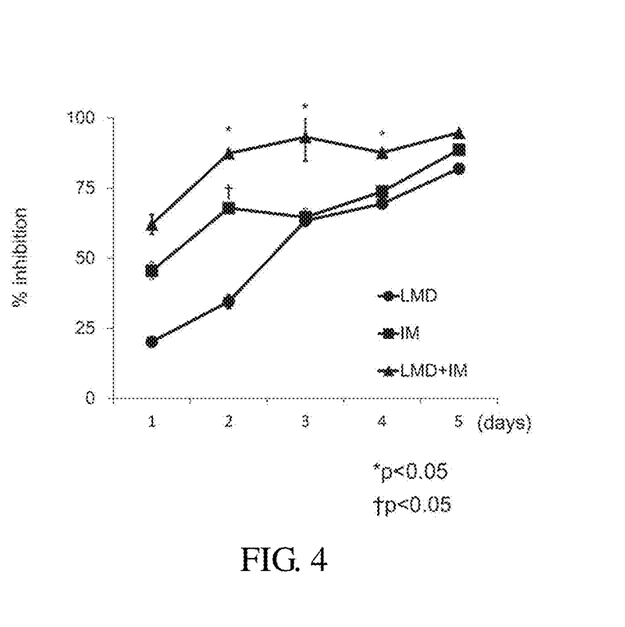
FIG. 4 shows results of measuring inhibition of $H^3$-thymidine uptake in the lenalidomide high sensitive Ph+ALL strain (KOPN57bi) in the presence of lenalidomide (LMD, 20 μM) alone, imatinib (IM, 0.5 nM) alone or combination thereof over time.

Time Course Study on Effect in Combination of Lenalidomide with Imatinib by Using a $H^3$-Thymidine Uptake Method (FIG. 4)

Ph+ALL strain (KOPN57bi) were cultured in the presence of 20 μM LMD alone, 0.5 μM IM alone or combination thereof for 1 to 5 days. Effect in the combination was recognized from 2 days in the culture, and % inhibition reached to 90% or more on 3 days in the culture.

Example 4

Figure 5:
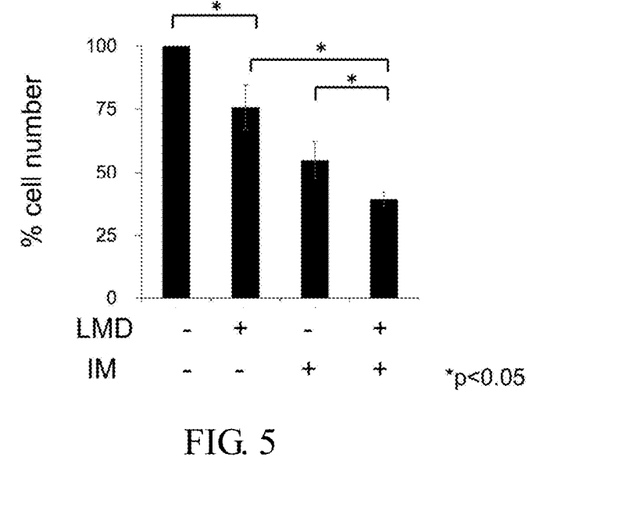
FIG. 5 shows results of calculating % of viable cell number (control is set to 100% by an alamar blue method) when the lenalidomide high sensitive Ph+ALL cell strain (KOPN57bi) was cultured in the presence of lenalidomide (LMD, 20 μM) alone, imatinib (IM, 0.5 nM) alone or combination thereof for 3 days.

Study on Living Cells by Using an Alamar Blue Method (FIG. 5)

Ph+ALL cell strain (KOPN57bi) were cultured in the presence of LMD (20 μM) alone or IM (0.5 μM) alone or combination thereof for 3 days, and then the number of viable cells was calculated by using an alamar blue method. As a result, the number of the viable cells mildly decreased in the case of the compound alone. However, the number of viable cells remarkably decreased in the combination thereof (FIG. 5).

Example 5

Figure 6:
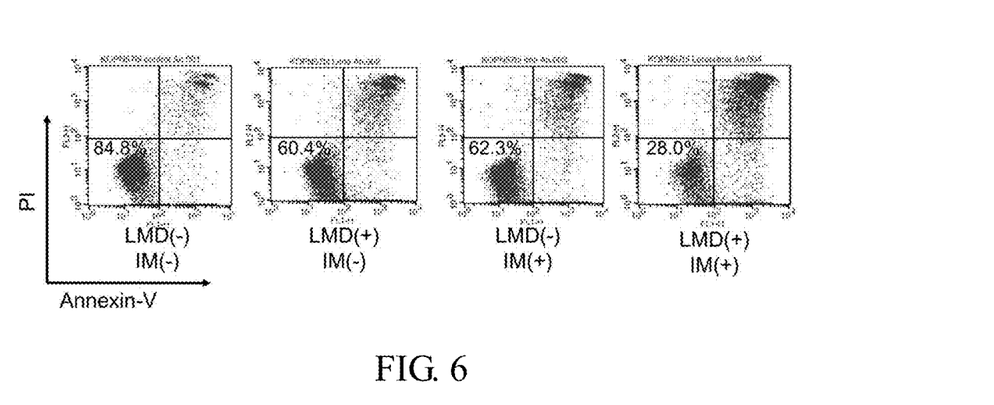
FIG. 6 shows graphs showing cell death induction rate by using flow cytometry with an Annexin V/propidium iodide (PI) double staining method after incubating the lenalidomide high sensitive Ph+ALL cell strain (KOPN57bi) in the present of lenalidomide (LMD, 20 μM) alone, imatinib (IM, 0.5 nM) alone or combination thereof for 3 days. Lower left regions show viable cells, and numerals show survival rate.

Study on Cell Death by Using an Annexin V/Propidium Iodide (PI) Double Staining Method (FIG. 6)

At an early stage of cell death, specific phospholipids are exposed on the cell membrane. By labeling Annexin V, which strongly binds to the phospholipid, with a fluorescent dye, rate of the early cell death can be detected by using flow cytometry. On the other hand, at a late stage of cell death, cell membrane/nuclear membrane is partially destroyed. Therefore, propidium iodide (PI), which is DNA-binding dye, can bind to nuclear DNA at the late stage of the cell death, and rate of the late cell death can be detected by using flow cytometry with PI staining Ph+ALL cell strain (KOPN57bi) were cultured in the presence of LMD (20 μM) alone, IM (0.5 μM) alone or combination thereof for 3 days. By using the Annexin V/PI double staining method, viable cell fraction (Annexin V-, PI-) showed 84.8% without the compounds and about 60% with the compound alone. However, it was reduced to 28.0% with the combination.

Example 6

Figure 7:
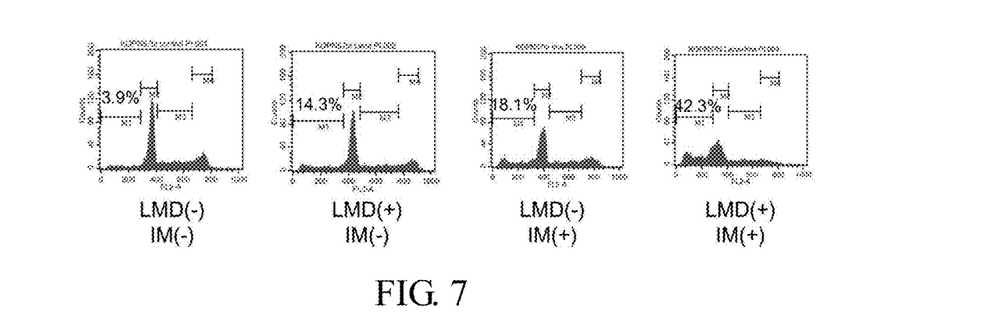
FIG. 7 shows graphs showing cell turnover and cell death by using flow cytometry with PI staining after culturing the lenalidomide high sensitive Ph+ALL cell strain (KOPN57bi) in the presence of lenalidomide (LMD, 20 μM) alone, imatinib (IM, 0.5 nM) alone or combination thereof for 3 days. Numerals show proportion of low diploid (apoptotic fractions).

Study on Cell Turnover by Using a PI Staining Method (FIG. 7)

When PI staining is performed under the condition that the cell membrane/nuclear membrane is fixed with a drug and PI can freely bind to intranuclear DNA, staining intensity changes depending on amount of DNA. Thus, cell turnover stop phase (G0/G1 phase, 2N), DNA synthesis phase (S phase, 2N→4N), pre-cell division phase (G2 phase, 4N) and cell division phase (M phase, 4N→2N) can be distinguished each other by using flow cytometry. In addition, when the cell death is induced by apoptosis, a cell fraction that DNA amount decreases by DNA cleavage (less than 2N) from the G0/G1 phase is detected. Ph+ALL cell strain (KOPN57bi) was cultured in the presence of LMD (20 μM) alone or IM (0.5 μM) alone or the combination thereof for 3 days, and then the PI staining was performed. In only the compound alone, a decrease of S phase fraction and a mild increase of apoptotic fraction were shown. On the other hand, in the combination, it was shown that proportion of all living cell fractions decreased while the apoptotic fraction remarkably increased to 42.3%.

Example 7

Figure 8:
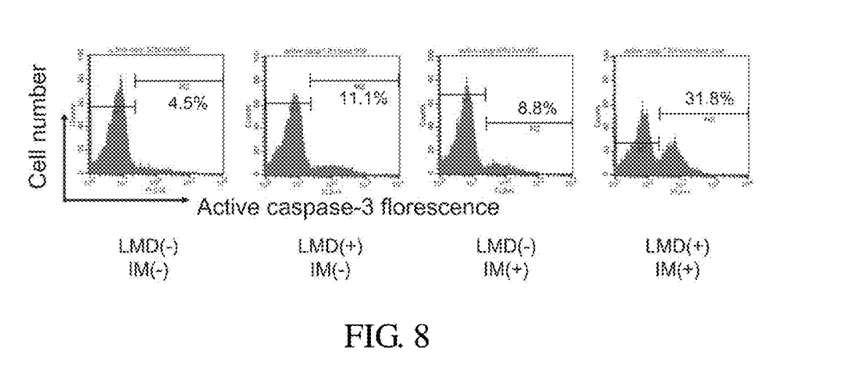

Study on Apoptosis by Using an Active Caspase-3 Antibody (FIG. 8)

Ph+ALL cell strain (KOPN57bi) was cultured in the presence of LMD (20 μM) alone or IM (0.5 μM) alone or combination thereof for 3 days. After fixation of cell membrane, the cells were stained with anti-active caspase-3 antibodies and positive cells were investigated by using flow cytometry. Numerals shows active caspase-3 positive rate. In the case of LMD or IM alone, positive rate was slightly increased as compared with no addition of the compound. On the other hand, in the combination of LMD with IM, 31.8% positive rate was shown.

Example 8

Study on Cell Death and Cell Turnover in LMD Low Sensitive Ph+ALL Cell Strain by Using an Annexin V/PI Double Staining Method (FIG. 9)

Figure 9A:
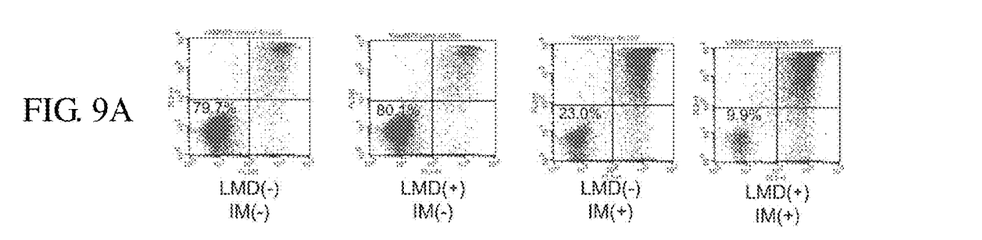
FIGS. 9A and 9B show graphs showing cell death induction rates using an Annexin V/propidium iodide (PI) double staining method (FIG. 9A) and cell turnover/cell death induction using PI staining (FIG. 9B) by using flow cytometry after culturing the lenalidomide low sensitive Ph+ALL strain (YAMN73) lacking IKZF1 exons 2-7 in the presence of lenalidomide (LMD) alone, imatinib (IM) alone or in combination thereof for 3 days. Numerals in FIG. 9A show survival rate, and numerals in FIG. 9B show proportion of low diploid (apoptotic fractions). Cell death was strongly induced by the combination of lenalidomide and imatinib even for the lenalidomide low sensitive strain.
Figure 9B:
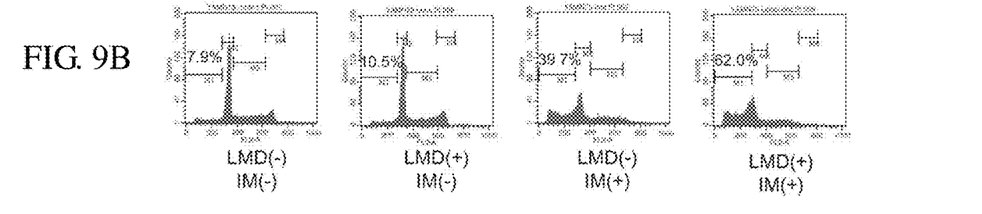

Lenalidomide low sensitive Ph+ALL strain (YAMN73) was used to be cultured in the presence of lenalidomide (LMD) alone, imatinib (IM) alone or combination thereof for 3 days. By using flow cytometry, cell death induction rates were calculated by using the Annexin V/propidium iodide (PI) double staining method (FIG. 9A) and cell turnover/cell death induction was investigated by using the PI staining (FIG. 9B). FIG. 9 shows the results, from the left, with control, lenalidomide (LMD) alone, imatinib (IM) alone, and combination of lenalidomide with imatinib. Numerals in FIG. 9A indicate survival rate. Numerals in FIG. 9B indicate proportion of the low diploid (apoptotic fraction). The cell death was strongly induced in the combination with the imatinib even when the lenalidomide low sensitive strain was used.

Example 9

Figure 10A:
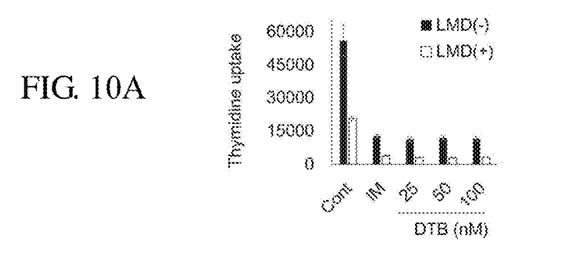
Figure 10B:
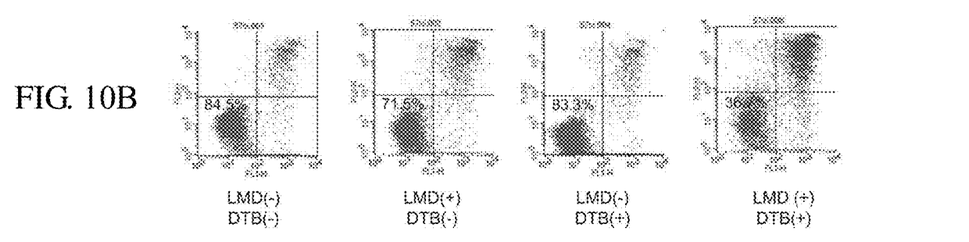
FIG. 10B shows graphs showing cell death induction rate by using flow cytometry with an Annexin V/propidium iodide (PI) double staining method after incubating the lenalidomide high sensitive Ph+ALL cell strain (KOPN57bi) in the present of lenalidomide (LMD) alone, dasatinib (DTB) alone or combination thereof for 3 days. Lower left regions show viable cells, and numerals show survival rate.

Study Using Tyrosine Kinase Inhibitor Dasatinib (FIGS. 10A and B)

FIGS. 10A and 10B show results of effect of dasatinib (DTB) which is a TKI other than imatinib. FIG. 10A shows a result of thymidine uptake after culturing the lenalidomide high sensitive Ph+ALL cell strain (KOPN57bi) in the presence of dasatinib (DTB, 20, 50, 100 nM) or imatinib (IM, 0.5 nM) for 3 days. FIG. 10B shows graphs showing cell death induction rate by flow cytometry with the Annexin V/propidium iodide (PI) double staining method after incubating the lenalidomide high sensitive Ph+ALL cell strain (KOPN57bi) in the present of lenalidomide (LMD, 20 µM) alone, dasatinib (DTB, 50 nM) alone or combination thereof for 3 days. FIG. 10B shows the results, from the left, with control, lenalidomide (LMD) alone, dasatinib (DTB) alone, and combination of lenalidomide with dasatinib. Lower left regions show viable cells, and numerals show survival rate. The combination of dasatinib with lenalidomide strongly induced cell death.

Example 10

Figure 11:
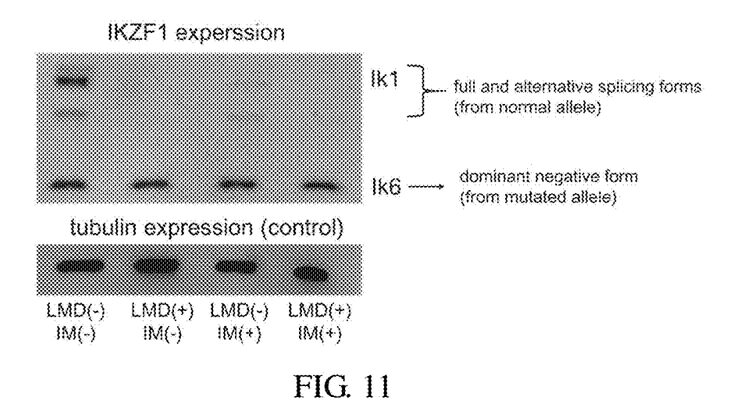

Study on Change of IKZF1 Expression by Using a Western Blotting Method (FIG. 11)

FIG. 11 shows change in expression of IKZF1 protein using western blotting method after culturing the lenalidomide high sensitive Ph+ALL cell strain (KOPN57bi) in the presence of lenalidomide (LMD, 20 µM) alone, imatinib (IM, 0.5 nM) alone or combination thereof for 24 hours. No change was observed in expression of dominant-negative isoform (Ik 6) under the above conditions, whereas expressions of normal allele-derived normal IKZF1 protein (including splicing isoform) was completely found by addition of lenalidomide.

Example 11

Figure 12:
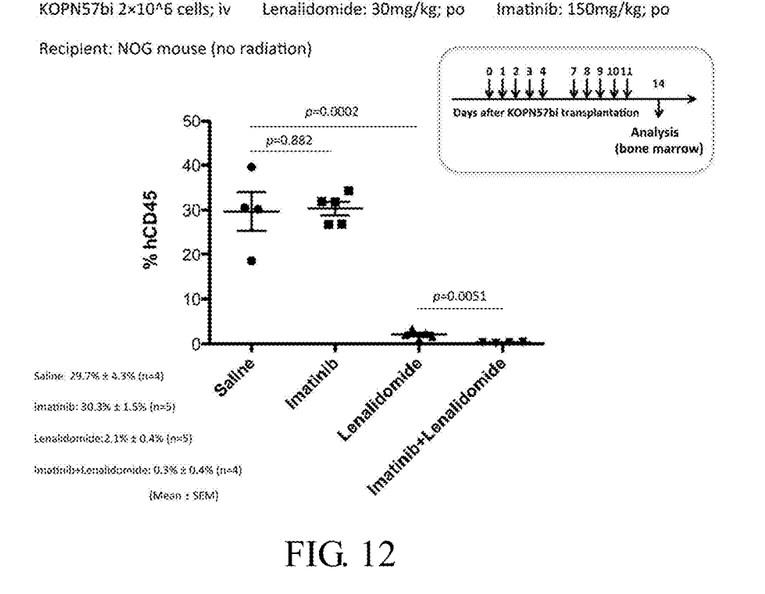
FIG. 12 shows a graph showing ratio of human CD45-positive cells in NOG mouse bone marrow mononuclear cells 2 weeks after administration of physiological saline, administration of lemalidomide (30 mg/kg, PO) alone, administration of imatinib (150 mg/kg, PO) alone, combined administration of LMD/imatinib to NOD/SCID/γnull (NOG) mouse in which the Ph+ALL cell strain (KOPN57bi) was administered.

Study by Using Immunodeficient Mice In Vivo (FIG. 12)

NOD/SCID/γ null mouse (NOG mouse) is widely used for research as immunodeficient mouse capable of efficiently transplanting human hematopoietic stem cells or tumor cells. A mouse transplanted with human leukemia cells is a system that can study therapeutic effect of a drug on human leukemia cells in the mouse body (in vivo). $2 \times 10^6$ cells of Ph+ALL cell strain (KOPN57bi) were administered to tail vein of the mice. The mice were divided into saline administration group, administration group of LMD alone (LMD 30 mg/kg/day), administration group of imatinib (IM) alone (150 mg/kg/day), administration group of combination of LMD with IM (LMD 30 mg/kg/day, Imatinib 150 mg/kg/day) (4 mice in each group). The mice were observed over time. Proportion of Ph+ALL cells in mononuclear cell fraction was investigated by using flow cytometry after isolating mononuclear cell fraction from mouse bone marrow blood two weeks after administration and staining with anti-human CD45 antibody binding to human leukemia cells. Approximately 30% of Ph+ALL cells were observed in the group treated with saline, and no effect was observed in the group treated with imatinib alone, whereas it decreased to 2.1% in the group administered with LMD alone (p=0.002). In the administration group of the combination, it was further reduced to 0.3% (p=0.0051). This result indicates that the administration of LMD and imatinib in combination strongly induces the cell death not only in vitro but also in mouse (in vivo).

CONCLUSION

To summarize the above results, it was revealed that the administration of LMD and imatinib in combination showed strong cell death-inducing effect on human Ph+ALL cells both in vitro and in vivo. A pharmaceutical composition using LMD and imatini in combination is an excellent pharmaceutical composition capable of remarkably improving treatment result of Ph+ALL patients, and the use of the combination of LMD with imatinib is an excellent treatment method.

We claimed:

1. A pharmaceutical composition for treating Philadelphia chromosome positive lymphocytic leukemia, comprising a BCR-ABL tyrosine kinase inhibitor and a thalidomide derivative,
    wherein the thalidomide derivative is lenalidomide and/or pomalidomide, and
    the BCR-ABL tyrosine kinase inhibitor is at least one selected from the group consisting of imatinib, dasatinib, nilotinib and bostinib.

2. The pharmaceutical composition according to claim 1, wherein the Philadelphia chromosome positive lymphocytic leukemia has an IKZF1 gene mutation.

3. The pharmaceutical composition according to claim 2, wherein the IKZF1 gene mutation lacks one or more exons.

4. The pharmaceutical composition according to claim 2, wherein the IKZF1 gene mutation lacks at least four exons.

5. The pharmaceutical composition according to claim 2, wherein the IKZF1 gene mutation is a single allelic mutation.

6. The pharmaceutical composition according to claim 1, wherein the Philadelphia chromosome positive lymphocytic leukemia is Philadelphia chromosome positive acute lymphocytic leukemia.

* * * * *